United States Patent
Govari et al.

(10) Patent No.: US 11,369,311 B1
(45) Date of Patent: Jun. 28, 2022

(54) VISUALIZING EMULSIFICATION IN 4D USING SCHLIEREN IMAGING

(71) Applicant: JOHNSON & JOHNSON SURGICAL VISION, INC., Santa Ana, CA (US)

(72) Inventors: Assaf Govari, Haifa (IL); Yehuda Algawi, Binyamina (IL); Amit Fuchs, Hogla (IL); Eran Aharon, Haifa (IL); Ilya Sitnitsky, Nahariya (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 0 days.

(21) Appl. No.: 17/130,459

(22) Filed: Dec. 22, 2020

(51) Int. Cl.
| A61B 5/00 | (2006.01) |
| H04N 13/282 | (2018.01) |
| H04N 13/207 | (2018.01) |
| H04N 13/254 | (2018.01) |
| A61F 9/007 | (2006.01) |
| A61B 3/14 | (2006.01) |

(52) U.S. Cl.
CPC ............ *A61B 5/4848* (2013.01); *A61B 3/145* (2013.01); *A61B 5/0073* (2013.01); *A61F 9/00745* (2013.01); *H04N 13/207* (2018.05); *H04N 13/254* (2018.05); *H04N 13/282* (2018.05)

(58) Field of Classification Search
CPC ..... A61B 5/4848; A61B 3/145; A61B 5/0073; A61F 9/00745; H04N 13/207; H04N 13/254; H04N 13/282
See application file for complete search history.

(56) References Cited

U.S. PATENT DOCUMENTS

| 5,463,593 | A | * | 10/1995 | Zanelli | G01H 9/00 367/13 |
| 6,142,382 | A | * | 11/2000 | Ting | B22F 9/082 239/433 |
| 11,230,996 | B2 | * | 1/2022 | Solomon | F02K 7/02 |
| 2006/0236525 | A1 | * | 10/2006 | Sliwa | B23K 26/351 29/594 |
| 2009/0093750 | A1 | * | 4/2009 | Herman | A61M 3/0283 606/107 |
| 2014/0267781 | A1 | * | 9/2014 | Buckner | G01N 21/45 348/241 |

(Continued)

FOREIGN PATENT DOCUMENTS

EP 3109613 A1 12/2016

OTHER PUBLICATIONS

Packer et al., "The physics of phaco: A review", J Cataract Refract Surg 2005; 31:424-431.

(Continued)

*Primary Examiner* — Jared Walker
(74) *Attorney, Agent, or Firm* — Tamara Evans (57) ABSTRACT

An apparatus includes a schlieren imaging assembly and a processor. The schlieren imaging assembly includes one or more two-dimensional (2D) schlieren imaging systems and is configured to acquire two-dimensional (2D) schlieren images of turbulence occurring in fluid media from a plurality of viewing angles. The processor is configured to produce, from the 2D schlieren images, a time-series of three-dimensional (3D) schlieren images corresponding to respective time instances.

14 Claims, 4 Drawing Sheets

(56) References Cited

U.S. PATENT DOCUMENTS

| | | | | |
|---|---|---|---|---|
| 2015/0016690 A1* | 1/2015 | Freeman | ............... | G06T 7/20 |
| | | | | 382/107 |
| 2015/0048264 A1* | 2/2015 | Sun | ............... | G01N 21/455 |
| | | | | 250/564 |
| 2016/0296769 A1* | 10/2016 | Barthe | ............... | A61N 7/02 |
| 2016/0327776 A1* | 11/2016 | Tsia | ............... | G02B 21/367 |
| 2017/0082124 A1* | 3/2017 | Kremeyer | ............... | F15D 1/0075 |
| 2017/0196453 A1* | 7/2017 | Papac | ............... | A61F 9/008 |
| 2017/0315564 A1* | 11/2017 | Thomas | ............... | B64C 13/18 |
| 2018/0188167 A1* | 7/2018 | Schoegl | ............... | H04N 17/02 |
| 2018/0269080 A1* | 9/2018 | Schwab | ............... | H01L 21/67051 |
| 2021/0316844 A1* | 10/2021 | Fasel | ............... | B64C 30/00 |
| 2022/0021801 A1* | 1/2022 | Kasumi | ............... | A61B 1/00006 |

OTHER PUBLICATIONS

Serafino et al., "Schlieren visualization of fluid dynamics phenomena during phacosonication in cataract surgery," Proc. SPIE 5580, 26th International Congress on High-Speed Photography and Photonics, (Mar. 17, 2005).

Mehta et al., The Art of Phacoemulsification, New Delhi, Jaypee Brothers, 2001, pp. 45-50.

Atcheson B., et al., "Time-resolved 3d Capture of Non-stationary Gas Flows", Acm Transactions on Graphics, 2008, vol. 27(5), pp. 1-10.

Kotaro O., "Measuring Rectilinear Flow within the Anterior Chamber in Phacoemulsification Procedures," Journal of Cataract and Refractive Surgery, 2004, vol. 30 (8), pp. 1759-1767.

Serafino G., et al., "Schlieren Visualization of Fluid Dynamics Phenomena during Phacosonication in Cataract Surgery", Proc. SPIE 5580, 26th International Congress on High-Speed Photography and Photonics, Mar. 17, 2005, 1 page.

Tognetto D., et al., "Visualization of Fluid Turbulence and Acoustic Cavitation During Phacoemulsification", Journal of Cataract and Refractive Surgery, 2005, vol. 31(2), pp. 406-411.

* cited by examiner

VISUALIZING EMULSIFICATION IN 4D USING SCHLIEREN IMAGING

FIELD OF THE INVENTION

The present invention relates generally to testing of medical systems that use piezoelectric-vibration, and particularly to optical inspection of phacoemulsification.

BACKGROUND OF THE INVENTION

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency which is thought to cause local shock waves in the capsular bag media, which emulsify the cataract. At a same time, a pump aspirates particles and fluid from the eye through the tip. Aspirated fluids are replaced with irrigation of a balanced salt solution to maintain the anterior chamber of the eye. After removing the cataract with phacoemulsification, the softer outer lens cortex is removed with suction. An intraocular lens (IOL) is then introduced into the empty lens capsule restoring the patient's vision.

Various observations of turbulence in fluid were reported in the scientific medical literature. For example, Davis P. reported in, The Art of Phacoemulsification, New Delhi, Jaypee Brothers, 2001, pages 45-50, Mehta K R, Alpar J J, editors, that phaco-surgeons often notice cataract tissue breakdown anterior to their phaco-needles without the tip touching the cataract, because the shock waves are focused in front of the phaco-needle, as shown by schlieren imaging.

Gabriella Serafino et al., reported in, "schlieren visualization of fluid dynamics phenomena during phaco-sonication in cataract surgery", Proc. SPIE 5580, 26th International Congress on High-Speed Photography and Photonics, (17 Mar. 2005), of an expanded and collimated laser diode beam that trans-illuminates a transparent tube containing a liquid medium. A machine is activated, separating the different phases of irrigation, aspiration and phaco-sonication. Fluid turbulences and phenomena related to the tip vibration constitute the phase images, visualized using schlieren or similar techniques. The optical Fourier transform is filtered by a blade or by a black dot. The filtered transform is reconstructed into the visualized phase image and this is acquired by a digital image processing system.

SUMMARY OF THE INVENTION

An embodiment of the present invention that is described hereinafter provides an apparatus including a schlieren imaging assembly and a processor. The schlieren imaging assembly includes one or more two-dimensional (2D) schlieren imaging systems and is configured to acquire two-dimensional (2D) schlieren images of turbulence occurring in fluid media from a plurality of viewing angles. The processor is configured to produce, from the 2D schlieren images, a time-series of three-dimensional (3D) schlieren images corresponding to respective time instances.

In some embodiments, the schlieren imaging assembly includes a plurality of the 2D schlieren imaging systems that are positioned at the plurality of viewing angles relative to the fluid media.

In some embodiments, the schlieren imaging assembly includes a 2D schlieren imaging system that is repositionable at the plurality of viewing angles relative to the fluid media.

In an embodiment, the processor is further configured to display the time-series of 3D schlieren images in video.

In another embodiment, at least one of the 2D schlieren imaging systems includes a lens or a mirror, a knife-edge and a camera, the lens or mirror configured to focus a laser beam onto the knife-edge, the knife-edge configured to semi-block the focused laser beam, and the camera configured to image the turbulence by capturing an image of the semi-blocked laser beam.

In some embodiments, the turbulence in the fluid media is caused by a vibrating needle of a phacoemulsification probe. In other embodiments, the turbulence in the fluid media is caused by a focused ultrasound beam.

In some embodiments, the apparatus further includes a modulated illumination source for stroboscopic operation, wherein the one or more two-dimensional (2D) schlieren imaging systems are configured to acquire the schlieren images in a stroboscopic mode.

In an embodiment, the schlieren imaging assembly includes a light source configured to emit an optical beam, and a beam splitter configured to split the optical beam from the light source, for acquiring at least two two-dimensional (2D) schlieren images simultaneously.

There is additionally provided, in accordance with another embodiment of the present invention, a method including acquiring two-dimensional (2D) schlieren images of turbulence occurring in fluid media from a plurality of viewing angles, using one or more 2D schlieren imaging systems. A time-series of three-dimensional (3D) schlieren images is produced, from the 2D schlieren images, corresponding to respective time instances.

The present invention will be more fully understood from the following detailed description of the embodiments thereof, taken together with the drawings in which:

DETAILED DESCRIPTION OF EMBODIMENTS

OVERVIEW

A phacoemulsification system typically drives a piezoelectric actuator included in a phacoemulsification probe/handpiece to vibrate a needle of the phacoemulsification probe during a cataract procedure. The needle may vibrate in one or more modes, where each mode has a given "natural" resonant frequency. Such a multi-resonance mode might yield, for example, a complex vibration trajectory that combines longitudinal, transverse, and torsion vibrations, each with its own resonant frequency. This mode may have a complex customizable vibration profile that may allow a physician to better perform phacoemulsification.

Evaluating the clinical efficacy of needle vibration is not straightforward. While the power input, and the amplitude of vibration of the emulsifier needle, may both be measured, this does not, in and of itself, predict how well needle vibration is transferred to a cataracted lens being emulsified. For example, the ocular media in which the needle vibrates induces changes in the mechanical load on the needle, and this causes the vibration frequencies to drift away from resonance, which in turn may lead to changes in needle trajectory and efficiency of power transfer.

One way to estimate an efficiency of power transfer is to visualize the turbulence induced in a fluid media by the vibrating needle, using, for example, a schlieren system to provide such visualization in 2D. However, such a 2D "snap-shot" provides limited information on the predicted quality of the emulsification.

Embodiments of the present invention that are described hereinafter provide methods and apparatuses to visualize a turbulent media in four-dimensions (4D: time plus three spatial dimensions), building mainly on schlieren imaging techniques. Specifically, the apparatuses perform 4D schlieren imaging of a turbulence in a fluid caused by a vibrating needle in the fluid, or by focusing an ultrasound beam into the fluid, (e.g., 4D visualization of density inhomogeneity generated in a material that is being emulsified). However, it should be understood that other phase contrast imaging techniques may be used instead of schlieren imaging, which are covered by embodiments of the invention.

In some embodiments, an apparatus is provided, comprising a schlieren imaging assembly comprising one or more two-dimensional (2D) schlieren imaging systems. In the present context, the term "schlieren imaging system" (or "schlieren system" for brevity) refers to any system that passes light through the media being imaged, and then focuses the light onto a focal plane, optical-spatially filters (e.g., generates the derivative of) the light wave with respect to phase at the focal plane and acquires the resulting image.

The schlieren imaging assembly is configured to acquire two-dimensional (2D) schlieren images of turbulence occurring in fluid media from a plurality of viewing angles. A processor of the apparatus is configured to produce, from the 2D schlieren images, a time-series of three-dimensional (3D) schlieren images corresponding to respective time instances.

In an embodiment, the processor is further configured to display the time-series of 3D schlieren images in video, so as to provide the aforementioned 4D schlieren imaging.

In one embodiment, the schlieren imaging assembly comprises a plurality of 2D schlieren imaging systems that are positioned at the plurality of viewing angles relative to the fluid media. The processor combines the respective plurality of acquired 2D images into a time-series of 3D images. Such an apparatus is therefore capable of producing a video of the 3D turbulence.

In another embodiment, the schlieren imaging assembly comprises a 2D schlieren imaging system that is repositionable at the plurality of viewing angles relative to the fluid media. For example, the schlieren imaging assembly can comprise a 2D schlieren system that is rotatable around the turbulent media. As the system rotates, it acquires 2D images of a steady state or slowly varying turbulence, in a rotating acquisition tomography mode. As another example, the sample and needle can be rotated, as one, inside a fixed schlieren system, which can also produce a rotating acquisition tomography mode.

Considering the 4D image quality in a setup comprising a plurality of schlieren systems that are positioned at the plurality of viewing angles, the accumulative time duration at which 2D images are acquired to produce a 3D image are negligible compared to the time constant of the turbulence, meaning that sharp 4D visualization is possible. While the accumulative time duration at which 2D images are acquired by a rotating setup might be long enough to affect 3D sharpness, a sufficiently slow turbulent pattern variance, along with an optional use of motion correction software tools, may enable a rotating 2D schlieren apparatus to produce a video clip of the 3D turbulence, i.e., to provide the aforementioned 4D schlieren imaging.

In some of the disclosed apparatuses, the vibrating needle is illuminated by a light source of the schlieren system(s) modulated (e.g., pulsed) at a frequency close to, but different from, that of the vibrating needle (e.g., in a stroboscope mode). The frequency difference slows the apparent motion of the needle, which allows the measurement of an actual trajectory performed by the needle.

The above types of 3D/4D visualization apparatuses may be used to improve designs of phacoemulsification probes as well as compare the effectiveness of different phacoemulsification probes.

SYSTEM DESCRIPTION

Figure 1:
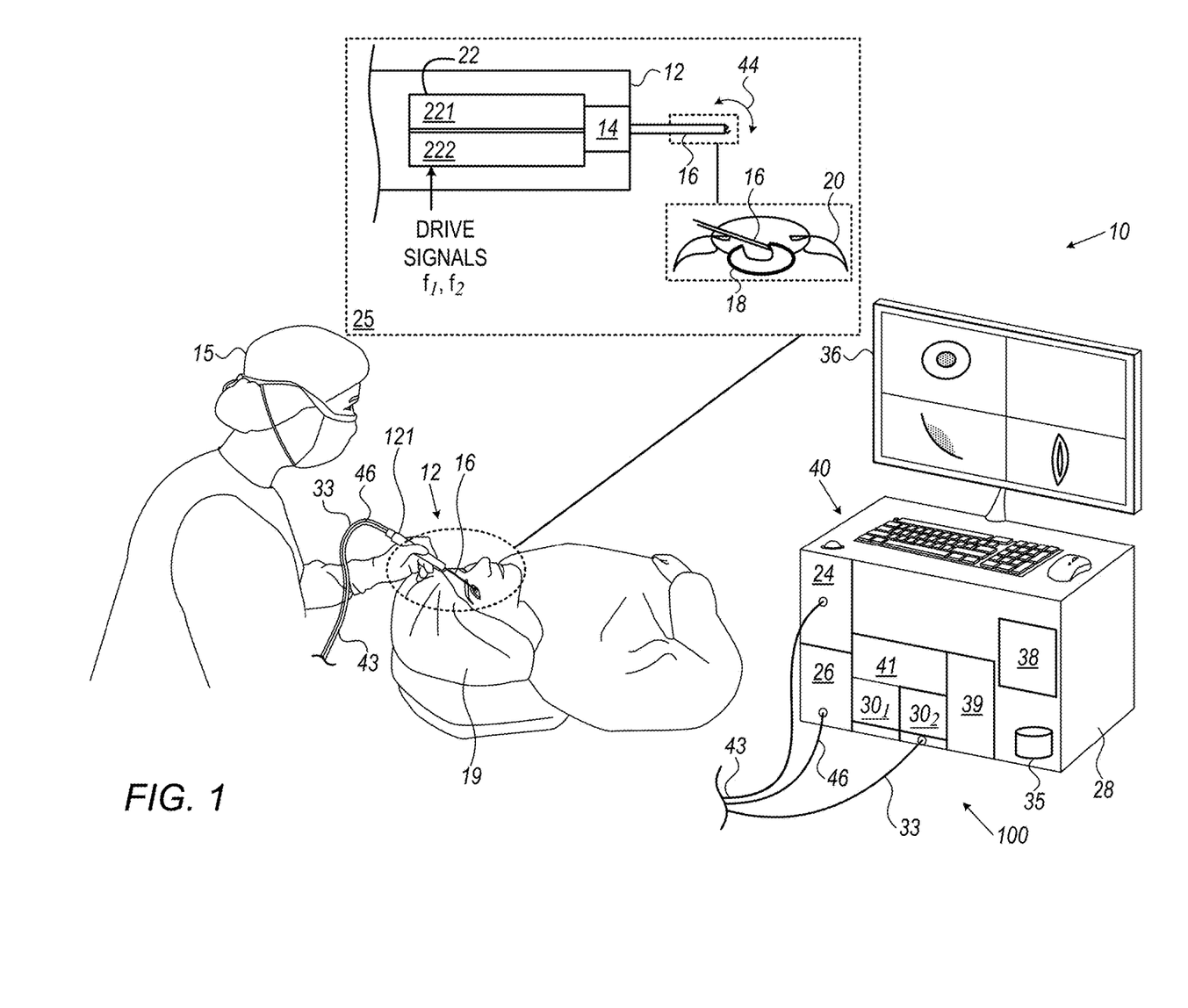
FIG. 1 is a pictorial view, along with a block diagram, of a phacoemulsification apparatus comprising a phacoemulsification probe, in accordance with an embodiment of the present invention.

FIG. 1 is a pictorial view, along with a block diagram, of a phacoemulsification apparatus 10 comprising a phacoemulsification probe 12, in accordance with an embodiment of the present invention. A clinical efficacy of probe 12 can be predicted using one of the 4D schlieren imaging apparatuses described in FIGS. 2 and 3 below.

As seen in the pictorial view of phacoemulsification apparatus 10, and the block diagram in inset 25, phacoemulsification probe 12 comprises a needle 16 configured for insertion into a lens capsule 18 of an eye 20 of a patient 19 by a physician 15. Needle 16 is coupled with a horn 14 comprised in probe 12, and is shown in inset 25 as a straight needle. However, any suitable needle may be used with the phacoemulsification probe 12, for example, a curved or bent tip needle commercially available from Johnson & Johnson Surgical Vision, Santa Ana, Calif., USA.

A piezoelectric actuator 22 inside probe 12 is configured to use piezoelectric crystals 221 and 222 to vibrate horn 14 and needle 16 in one or more resonant vibration modes of the combined horn and needle element. The vibration of needle 16 is used to emulsify a cataract during the phacoemulsification procedure by causing shock waves inside lens capsule 18.

In the shown embodiment, console 28 comprises a dual-channel piezoelectric drive system 100 comprising drive modules $30_1$ and $30_2$, each coupled, using electrical wiring running in cable 33, with each of the two piezoelectric crystals 221 and 222 of actuator 22. Drive-modules $30_1$ and $30_2$ are controlled by a processor 38 and convey processor-controlled driving signals via cable 33 to adjust frequencies of a multi-resonance mode of piezoelectric actuator 22 to maintain needle 16 at maximal vibration along a trajectory 44. Each of the drive modules may be realized in hardware or software, for example, in a proportional-integral-derivative (PID) control architecture.

Drive system 100 excites, using drive-modules $30_1$ and $30_2$, each of the crystals independently in a selected resonant mode, typically at different frequencies $f_1$ and $f_2$. For example, crystal 221 is vibrated in a longitudinal direction, whereas crystal 222 is vibrated in an axial direction. Since each of crystals 221 and 222 are required to vibrate only in one mode, there is less interaction between the modes, and thus it is much easier to generate and control the required vibrations. The disclosed apparatus for schlieren imaging enables to characterize and optimize trajectory 44 to yield best phacoemulsification with a given probe and driving system.

Processor 38 is further configured to use a switching circuitry 41 to connect drive modules $30_1$ and/or $30_2$ to vibrate needle 16 in one of several prespecified trajectories.

Some or all of the functions of processor 38 may be combined in a single physical component or, alternatively, implemented using multiple physical components. These physical components may comprise hard-wired or programmable devices, or a combination of the two. In some embodiments, at least some of the functions of processor 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

Processor 38 may receive user-based commands via a user interface 40, which may include setting a vibration mode and/or frequency of the piezoelectric actuator 22, adjusting the vibration mode and/or frequency of the piezoelectric actuator 22, setting or adjusting a stroke amplitude of the needle 16, setting or adjusting an irrigation and/or aspiration rate of the pumping sub-system 26. Additionally, or alternatively, processor 38 may receive user-based commands from controls located in handle 121 or in a foot pedal (not shown), to, for example, select trajectory 44, or another trajectory, for needle 16. In an embodiment, user interface 40 and display 36 may be combined in a touch screen graphical user interface.

In the shown embodiment, during the phacoemulsification procedure, a pumping sub-system 24 comprised in a console 28 pumps irrigation fluid from an irrigation reservoir to needle 16 to irrigate the eye. The fluid is pumped via a tubing line 43 running from the console 28 to the probe 12. In an alternative embodiment, irrigation fluid may be administered via a bottle using a gravity method known in the art. Waste matter (e.g., emulsified parts of the cataract) and eye fluid are aspirated via needle 16 to the collection receptacle by a pumping sub-system 26, also comprised in console 28, which uses tubing line 46 running from probe 12 to console 28. As seen in FIG. 1, processor 38 may present results of the procedure on a display 36.

The apparatus shown in FIG. 1 may include further elements, which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

While FIG. 1 shows a piezoelectric actuator 22 comprising two piezoelectric crystals, in general, piezoelectric actuator 22 may comprise one or more piezoelectric crystals. For example, piezoelectric actuator 22 may comprise three piezoelectric crystals, each of which vibrates needle 16 independently at a spatially different direction (e.g. longitudinal, axial, and torsional).

Figure 2:
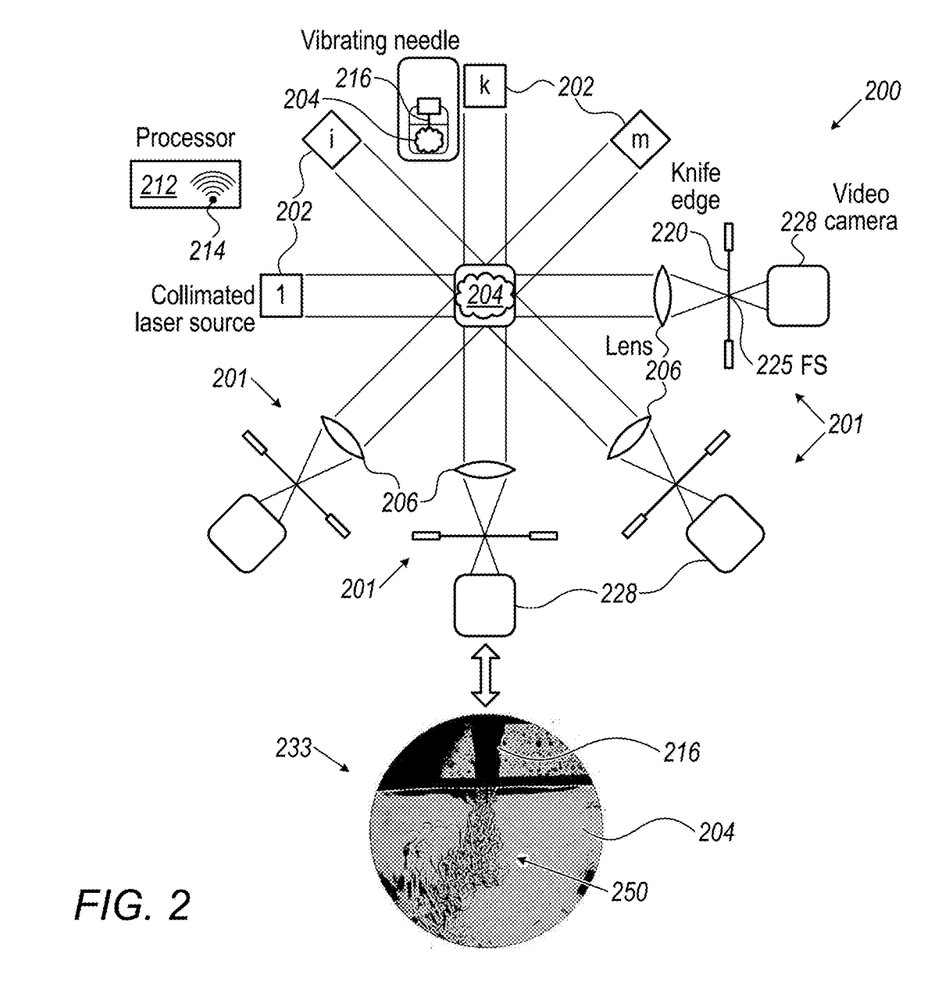
FIG. 2 is a pictorial top view, schematically illustrating an apparatus for 4D visualizing fluid turbulence caused by the vibration of the needle of the phacoemulsification probe of FIG. 1, in accordance with an embodiment of the present invention.

FIG. 2 is a pictorial top view, schematically illustrating an apparatus 200 for 4D visualizing fluid turbulence caused by the vibration of needle 16 of phacoemulsification probe 12 of FIG. 1, in accordance with an embodiment of the present invention. Apparatus 200 comprises a number m of 2D schlieren systems 201 (also numerated 1, i, k, . . . m) that are arranged equiangularly around turbulent media 204 (caused by vibration of needle 216).

Each 2D schlieren system 201 is capable of providing a 2D schlieren image, such as image 233. As seen, 2D image 233 shows needle 216, turbulent fluid media 204, and a phase-contrast view of turbulence 250 of media 204.

To capture a 2D schlieren image, each 2D schlieren system 201 comprises a collimated laser source 202 that generates a plane wave incident of turbulent media 204. The transmitted plane wave, which includes phase information of the turbulence, is focused (225) by a lens 206 onto a knife edge 220. A video camera 228 having suitable optics acquires the spatially filtered beam to generate an image such as image 233.

As noted above, laser sources 202 of the schlieren system(s) can be pulsed at a frequency close to, but different from, that of the vibrating needle 216 (e.g., in a stroboscope mode), to allow measurement of an actual trajectory performed by needle 216.

The components of apparatus 200 are controlled and synchronized in time by a processor 212, using wire links and/or wireless (214) links, depending on system design.

Apparatus 200 can simultaneously acquire 2D images from multiple angles, and therefore an acquisition time to generate a 3D image can be made negligible compared with the turbulence dynamics (e.g., $t_{aq.}$=10 mSec vs. $\tau$=1 Sec time constant of the turbulence). This means that apparatus 200 is capable of providing a time-series of three-dimensional (3D) schlieren images corresponding to respective time instances, and furthermore a high-quality 3D video movie (to create a 4D imaging) of the turbulence.

Figure 3:
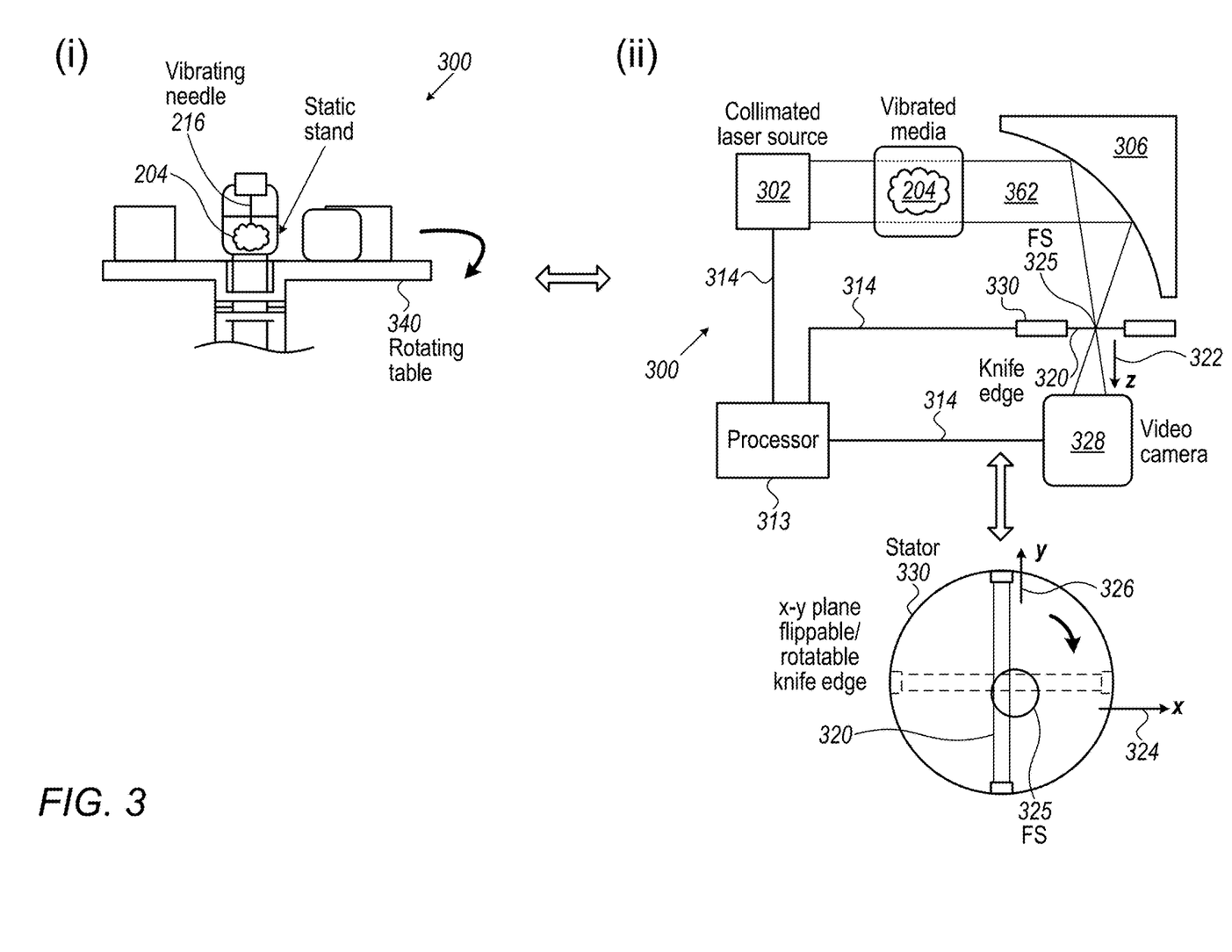
FIG. 3 is a pictorial view schematically illustrating an apparatus comprising a rotating schlieren system for 3D/4D visualization of fluid turbulence caused by the vibration of the needle of the phacoemulsification probe of FIG. 1, in accordance with another embodiment of the present invention.

FIG. 3 is a pictorial view schematically illustrating an apparatus 300 comprising a rotating schlieren system for 3D/4D visualizing fluid turbulence caused by the vibration of needle 16 of phacoemulsification probe 12 of FIG. 1, in accordance with another embodiment of the present invention.

A side view (i) of apparatus 300 shows a schlieren system (described in top view (ii) of FIG. 3), which is mounted on a rotatable table 340. Turbulent media 204 (caused by needle 216 vibration) is statically mounted at the center of rotation.

A top view (ii) of FIG. 3 shows that the rotating table-mounted 2D schlieren system comprises a collimated laser source 302 that generates a plane wave incident of turbulent media 204. The transmitted plane wave 362, which includes phase information of the turbulence, is focused (FS) (325) by a paraboloid mirror 306 onto a knife edge 320. The optical axis of propagation is defined as a z-axis 322. A video camera 328 having suitable optics acquires (e.g., over each acquisition time window $t_{aq}$) the spatially filtered beam to generate an image such as image 233 of FIG. 2.

During rotation, the rotating schlieren system acquires a set of 2D schlieren images, such as image 233 of FIG. 2, with the number of acquired 2D images over a half rotation being approximately $T/2t_{aq}$, with T/2 being a half rotation time of the system, and $t_{aq}$ being an acquisition time of a single 2D image.

In case of a steady-state or slowly varying pattern of the turbulence pattern, it may be possible to assume that (a) the acquisition time $t_{aq}$ is small compared to the half rotation time T/2, and (b) that the half-rotation time is small compared to the turbulence time constant, $\tau$, i.e. $t_{aq} \ll T/2 \ll \tau$ holds. As an example, assuming $t_{aq}$=10 mSec, T=0.1 Sec, and $\tau$=1 Sec, a clear tomographic visualization of the turbulence is possible.

The components of apparatus 300 are controlled and synchronized in time by a processor 313, so as to provide a time-series of three-dimensional (3D) schlieren images corresponding to respective time instances, and furthermore a high-quality 3D video movie (to create a 4D imaging) of the turbulence.

Control links used by processor 313 are shown as wire link 314, by way of example.

In yet another embodiment, two or more 2D schlieren systems may be mounted on a rotating table, so as to achieve improvement in temporal resolution. For example, two mutually orthogonal 2D schlieren systems improve the temporal resolution of the tomographic image by a factor of 2, as only a quarter of rotation, T/4, is required for 4D imaging. Three 2D schlieren systems mounted 60° one to the other improve the temporal resolution of the tomographic image by a factor of 3, as only a sixth rotation, T/6, is required for the 4D imaging. Note that with a sufficiently slowly varying turbulent pattern, apparatus 200, or an apparatus with enhanced temporal resolution, may be sufficient to produce a video film of the 3D turbulence, i.e., to provide the aforementioned 4D schlieren imaging.

In some embodiments, additional phase information may be acquired by a 2D schlieren system of any of the apparatuses of FIG. 2 and FIG. 3, by rotating or flipping the knife edge, for example, between two orthogonal orientations (e.g., x-axis 324, y-axis 326) within an x-y plane, normal to the axis z of propagation. To achieve a stable blade, a circumference driver stator 330 geometry may be used to rotate blade 320, while holding the blade on its two ends. As seen, half of FS 325 is blocked at each of the two orthogonal orientations.

The apparatuses shown in FIGS. 2 and FIG. 3 are brought purely by way of example. Other optical designs may be used, for example with guided optics.

Figure 4:
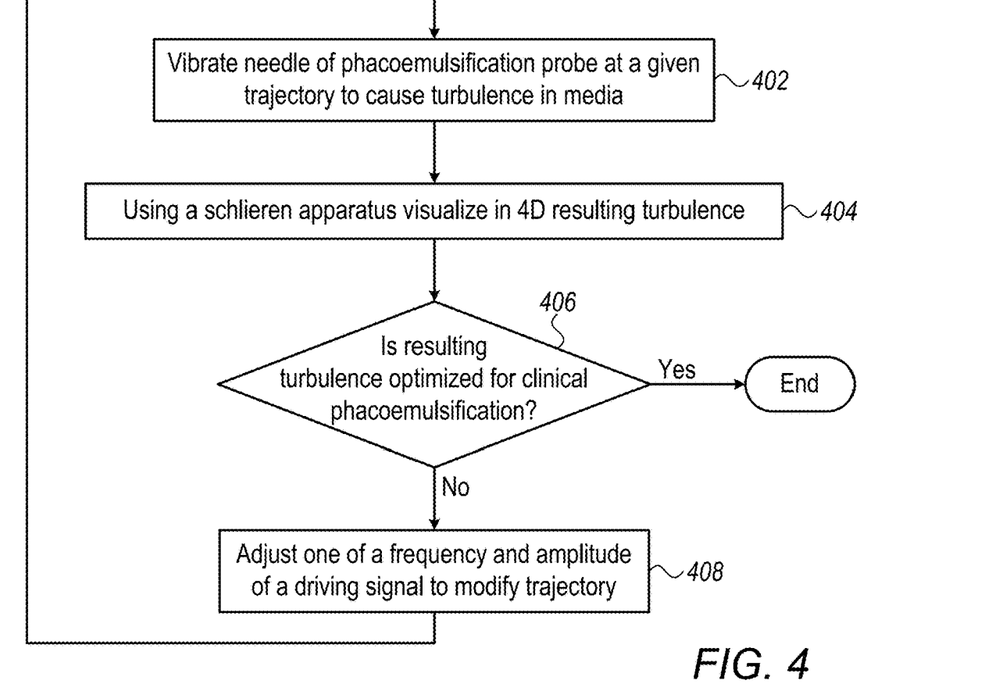
FIG. 4 is a flow chart schematically illustrating a method for 4D visualization of fluid turbulence caused by the vibration of the needle of the phacoemulsification probe of FIG. 1, in accordance with an embodiment of the present invention.

FIG. 4 is a flow chart schematically illustrating a method for 4D visualizing fluid turbulence 204 caused by the vibration of the needle of the phacoemulsification probe of FIG. 1, in accordance with an embodiment of the present invention. The algorithm, according to the presented embodiment, carries out a process that begins at a turbulence generation step 402, with vibrating needle 16 of phacoemulsification probe 12 at a given trajectory (e.g., trajectory 44) causing turbulence in media 204. To this end, one or more piezo crystals of probe 12 are typically driven at respective resonant modes of the crystals. Nevertheless, at least for testing purposes, the crystals may be driven in non-resonance modes.

At a schlieren imaging step 404, using one of the schlieren apparatuses of FIG. 2 or FIG. 3, the turbulence is visualized in 4D.

At a turbulence checking step 406, a user or a processor analyzes the resulting turbulence, for example, by watching a video of the turbulence generated in step 404. If the resulting turbulence is deemed optimized for clinical phacoemulsification, the process ends. Otherwise, at a vibration adjustment step 408, a user or a processor adjusts the needle vibration trajectory, for example, by adjusting either the frequency or amplitude of a driving signal, and the process returns to step 402.

The above process may end with a conclusion that the tested trajectory is not suitable, and another trajectory can then be selected and tested by steps 402-408. Further, the above process may end with a conclusion that the tested probe/needle design cannot yield sufficient clinical efficacy of vibration. An engineer watching the 4D imaging may then offer a different design.

The example flow chart shown in FIG. 4 is chosen purely for the sake of conceptual clarity. For example, additional steps such as visualizing the needle trajectory using a stroboscope mode of illumination are omitted for simplicity and clarity of presentation.

Figure 5:
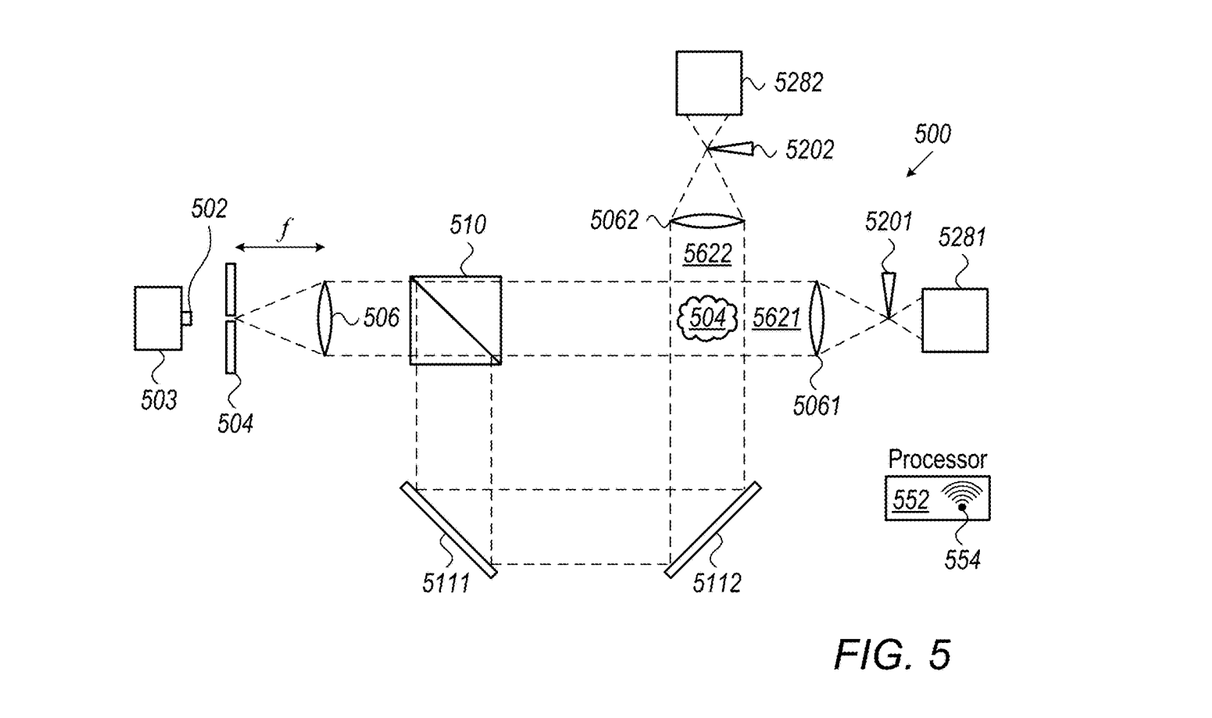
FIG. 5 is a pictorial top view, schematically illustrating an apparatus for 4D visualizing fluid turbulence caused by the vibration of the needle of the phacoemulsification probe of FIG. 1, in accordance with a further embodiment of the present invention.

FIG. 5 is a pictorial top view, schematically illustrating an apparatus 500 for 4D visualizing fluid turbulence caused by the vibration of the needle of the phacoemulsification probe of FIG. 1, in accordance with a further embodiment of the present invention.

To capture a 2D schlieren image, two 2D schlieren setups are used. The two setups have optical axes that are orthogonal to one another. Apparatus 500 comprises a bright monochromatic light source, such as LED 502 (thermally coupled to a heat sink 503) that together with a pinhole 504 and lens 506 forms a source of a plane wave incident on a beam splitter 510. A first wave is transmitted to incident turbulent media 504 from one direction. The split wave is reflected by mirrors 5111 and 5112 and incidents turbulent media 504 from an orthogonal direction to the first wave. The two transmitted orthogonal plane waves 5621 and 5622, which contain phase information of the turbulence, are focused by respective lenses 5061 and 5062 onto respective knife edges 5201 and 5202. Respective video cameras 5281 and 5282 having suitable optics acquire the spatially filtered orthogonal beams to generate a 3D image.

Using beam splitter 510 and beam folding mirrors 5111 and 5112 enables using a single light source to acquire, at the same time, two orthogonal two-dimensional (2D) schlieren images.

The components of apparatus 500 are controlled and synchronized in time by a processor 552, using wire links and/or wireless (554) links, depending on system design.

Apparatus 500 thus simultaneously acquire 2D images from two orthogonal directions, and therefore the acquisition time to generate a 3D image can be made negligible compared with the turbulence dynamics (e.g., $t_{aq}$=10 mSec vs. $\tau$=1 Sec time constant of the turbulence). This means that apparatus 500 is capable of providing a time-series of three-dimensional (3D) schlieren images corresponding to respective time instances, and furthermore a 3D video movie of the turbulence.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
a schlieren imaging assembly, which comprises one or more two-dimensional (2D) schlieren imaging systems and which is configured to acquire 2D schlieren images of turbulence occurring in fluid media from a plurality of viewing angles; and
a processor, which is configured to produce, from the 2D schlieren images, a time-series of three-dimensional (3D) schlieren images corresponding to respective time instances.

2. The apparatus according to claim 1, wherein the schlieren imaging assembly comprises a plurality of the 2D schlieren imaging systems that are positioned at the plurality of viewing angles relative to the fluid media.

3. The apparatus according to claim 1, wherein the schlieren imaging assembly comprises a 2D schlieren imaging system that is repositionable at the plurality of viewing angles relative to the fluid media.

4. The apparatus according to claim 1, wherein the processor is further configured to display the time-series of 3D schlieren images in video.

5. The apparatus according to claim 1, wherein at least one of the 2D schlieren imaging systems comprises a lens or a mirror, a knife-edge and a camera, the lens or mirror configured to focus a laser beam onto the knife-edge, the knife-edge configured to semi-block the focused laser beam, and the camera configured to image the turbulence by capturing an image of the semi-blocked laser beam.

6. The apparatus according to claim 1, wherein the turbulence in the fluid media is caused by a vibrating needle of a phacoemulsification probe.

7. The apparatus according to claim 1, wherein the turbulence in the fluid media is caused by a focused ultrasound beam.

8. The apparatus according to claim 1, further comprising a modulated illumination source for stroboscopic operation, wherein the one or more 2D schlieren imaging systems are configured to acquire the 2D schlieren images in a stroboscopic mode.

9. The apparatus according to claim 1, wherein the schlieren imaging assembly comprises a light source configured to emit an optical beam, and a beam splitter configured to split the optical beam from the light source, for acquiring at least two 2D schlieren images simultaneously.

10. A method, comprising:
acquiring two-dimensional (2D) schlieren images of turbulence occurring in fluid media from a plurality of viewing angles, using one or more 2D schlieren imaging systems; and
producing, from the 2D schlieren images, a time-series of three-dimensional (3D) schlieren images corresponding to respective time instances.

11. The method according to claim 10, further comprising displaying the time-series of 3D schlieren images in video.

12. The method according to claim 10, wherein the turbulence in the fluid media is caused by a vibrating needle of a phacoemulsification probe.

13. The method according to claim 10, wherein the turbulence in the fluid media is caused by a focused ultrasound beam.

14. The method according to claim 10, wherein acquiring the schlieren images comprise illuminating the fluid media using a modulated illumination source for stroboscopic operation, and acquiring the schlieren images in a stroboscopic mode.

* * * * *